United States Patent [19]

Goswami et al.

[11] Patent Number: 4,927,927
[45] Date of Patent: May 22, 1990

[54] FLUORESCENT DYES AND BIOLOGICAL AND ANALYTICAL USES THEREOF

[75] Inventors: Ramanuj Goswami, Rochester; Chin H. Chen, Webster, both of N.Y.

[73] Assignee: Eastman Kodak Company, Rochester, N.Y.

[21] Appl. No.: 278,993

[22] Filed: Dec. 2, 1988

Related U.S. Application Data

[62] Division of Ser. No. 824,765, Jan. 31, 1986, Pat. No. 4,812,395.

[51] Int. Cl.$^5$ .................. C07C 97/18; C07C 50/22; C07C 50/38
[52] U.S. Cl. .................................................. 544/106
[58] Field of Search ............... 552/286, 287, 288; 544/101, 107, 111, 124, 146; 546/184, 195, 285; 548/528, 529; 549/29, 59

[56] References Cited

U.S. PATENT DOCUMENTS 4,036,859 7/1977 Ribaldone et al. .................. 260/364
4,296,043 10/1981 Schroeder ............................ 260/352

FOREIGN PATENT DOCUMENTS 508322 9/1930 Fed. Rep. of Germany ...... 552/286
178942 8/1935 Switzerland ........................ 552/286
277670 11/1928 United Kingdom ................ 552/286

OTHER PUBLICATIONS

Cooke et al., *Aust. J. Chem.*, 11, pp. 230–235 (1958).
Cooke et al., *Aust. J. Chem.* 28, pp. 1053–1057 (1975).
Cooke et al., *Aust. J. Chem.* 30, pp. 2241–2247 (1977).
Cooke et al., *Aust. J. Chem.*, 32, pp. 1841–1847 (1979).
Chaffee et al., *Aust. J. Chem.* 34, pp. 587–598 (1981).

*Primary Examiner*—Richard L. Raymond
*Assistant Examiner*—Raymond Covington
*Attorney, Agent, or Firm*—J. Lanny Tucker

[57] ABSTRACT

Substituted 4-oxo-4H-benz-[d,e]anthracenes are fluorescent dyes which are useful in biomedical studies and analytical determinations. They are particularly useful in assays for living organisms, e.g. microorganisms, carried out at a pH of 9 or less. For these determinations, the fluorescent dyes can be attached to reducible compounds which will release the dye upon reduction. Alternatively, these dyes can be used in assays for hydrolytic enzymes or biological cells containing these enzymes. For these determinations, the dyes are attached to blocking groups.

12 Claims, No Drawings

FLUORESCENT DYES AND BIOLOGICAL AND ANALYTICAL USES THEREOF

This is a division of application Ser. No. 824,765, filed Jan. 31, 1986, now U.S. Pat. No. 4,812,393.

FIELD OF THE INVENTION

This invention relates to substituted 4-oxo-4H-benz-[d,e]anthracenes which are fluorescent dyes. It also relates to novel reducible and hydrolyzable compounds derived from such dyes. Further, this invention relates to the use of such materials in biomedical studies and clinical chemistry. In particular, it relates to analytical compositions and elements useful in analytical methods for the determination of various biological species.

BACKGROUND OF THE INVENTION

There is a continuing need in various scientific and industrial fields for fluorescent dyes which exhibit high quantum efficiencies providing improved sensitivity. For example, the staining of biological tissues and cells with fluorescent dyes in order to differentiate one type from another or to render them more observable is well known in the art. Red fluorescent dyes are especially desirable because they are highly visible.

Further, chemical analysis of liquids, such as water, milk and biological fluids is often desirable or necessary for health maintenance and diagnostic care. Various compositions and elements to facilitate such analyses are known. Such materials generally include a reagent composition for determining a substance under analysis, identified as an "analyte" herein. The analyte can be a living organism, such as a microorganism or yeast cell, or a nonliving chemical substance. The reagent composition, upon interaction with the analyte, provides a detectable change (e.g. dye formation or dye release).

Recently, much work has been directed to developing compositions and elements which are useful for rapid and highly quantitative diagnostic or clinical analysis of biological fluids such as whole blood, sera, plasma, urine and the like. For example, for the rapid and effective diagnosis and treatment of infectious diseases, it is desirable to be able to detect the bacteria causing the disease as rapidly as possible. Infections of the urinary tract are among the most common bacterial diseases, second in frequency only to infections of the respiratory tract.

In U.S. Ser. No. 824,766 now U.S. Pat. No. 4,857,271, filed on even date herewith by Belly et al and entitled REDUCIBLE COMPOUNDS AND ANALYTICAL COMPOSITIONS, ELEMENTS AND METHODS UTILIZING SAME, novel reducible compounds are described and claimed which are useful in the detection of bacteria and other analytes. The assays of Belly et al provide colorimetric and fluorometric dyes in the presence of the analyte.

It is generally known that fluorescent dyes are more sensitive than colorimetric dyes in many biological assays. A variety of fluorescent dyes have been used in such assays, including the Belly et al assays. Such dyes include, for example, coumarins, fluorescein derivatives, phenalenones, benzphenalenones, spiroacridines and umbelliferone derivatives. Some of these dyes emit radiation in the red region of the spectrum. While the Belly et al assays represent a significant advance in the art, it would be useful to have additional dyes which have high quantum efficiencies and excellent sensitivity.

SUMMARY OF THE INVENTION

The present invention provides substituted or unsubstituted 4-oxo-4H-benz-[d,e]anthracene. These compounds are fluorescent dyes represented by the structure:

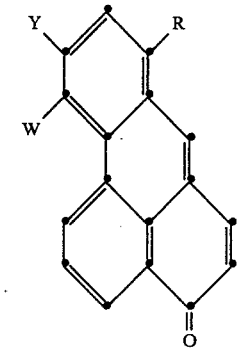

wherein R is hydrogen, substituted or unsubstituted alkyl, substituted or unsubstituted hydroxyalkyl or substituted or unsubstituted alkoxycarbonyl, W is hydrogen or an electron withdrawing group, and Y is hydrogen or a group comprised of a heteroatom having a lone pair of electrons or a negative charge with an associated cation.

This invention also provides a reducible compound of the structure $CAR\text{-}(-R^1)_n$ wherein CAR is a substituted or unsubstituted aromatic or quinone nucleus, n is 1 or 2, and $R^1$ comprises a moiety derived from the substituted or unsubstituted compound described above wherein R and W are as defined, and Y is hydroxy or mercapto.

Further, a hydrolyzable compound of this invention is represented by the structure:

BLOCK-X-R'-L wherein BLOCK is a hydrolyzable group, X is —O—, —NR'—, or —S—, R' is hydrogen, substituted or unsubstituted alkyl, substituted or unsubstituted cyclohexyl, substituted or unsubstituted phenyl or a substituted or unsubstituted heterocyclic group, R' is a moiety derived from the fluorescent compound described above wherein R, Y and W are as defined, and L is hydrogen or a specific binding ligand.

Moreover, this invention provides a dry analytical element for the determination of an analyte comprising an absorbent carrier material and containing either the reducible compound or the hydrolyzable compound described above.

A method for distinguishing cells in a biological sample comprises contacting the sample with the substituted or unsubstituted fluorescent compound described above.

Further, a method for the determination of an analyte in a liquid comprises the steps of:

A. contacting a sample of a liquid suspected of containing an analyte with either the reducible compound or the hydrolyzable compound described above to provide a fluorescent dye as a result of the presence of the analyte, and B. determining the fluorescent dye.

The fluorescent dyes of this invention exhibit high quantum efficiencies and thereby have high sensitivity when used to detect low levels of analytes. Preferred fluorescent compounds of this invention emit radiation in the red portion of the electromagnetic spectrum, i.e. they generally exhibit maximum fluorescence emission (i.e. $\lambda_{max}$) at a wavelength above about 600 nm.

DETAILED DESCRIPTION OF THE INVENTION

The novel fluorescent compounds of this invention are substituted 4-oxo-4H-benz-[d,e]anthracenes represented by the structure:

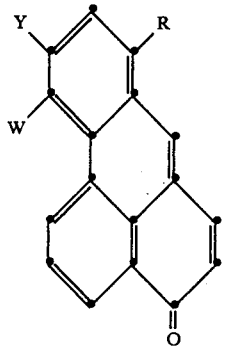

In this structure, R is hydrogen, substituted or unsubstituted alkyl (preferably of 1 to 12 carbon atoms, e.g. methyl, ethyl, isopropyl, benzyl, phenethyl, etc.), substituted or unsubstituted hydroxyalkyl (preferably of 1 to 12 carbon atoms, e.g. hydroxymethyl, 2-hydroxyethyl, 2-hydroxyisopropyl, etc.), or substituted or unsubstituted alkoxycarbonyl (preferably of 2 to 12 carbon atoms, e.g. methoxycarbonyl, ethoxycarbonyl, n-propoxycarbonyl, etc.). preferably, R is hydrogen, substituted or unsubstituted alkyl or substituted or unsubstituted alkoxycarbonyl, and more preferably, it is substituted or unsubstituted alkoxycarbonyl.

W is hydrogen or an electron withdrawing group as that term is understood in the art (i.e. a group generally having a positive Hammett sigma value as determined by standard procedures). Particularly useful electron withdrawing groups include, but are not limited to, halo (e.g. fluoro, chloro, bromo), cyano, carboxy, acyl, substituted or unsubstituted arylsulfonyl (preferably of 6 to 10 carbon atoms, e.g. phenylsulfonyl, tolylsulfonyl, etc.), substituted or unsubstituted alkylsulfonyl (preferably of 1 to 6 carbon atoms, e.g. methylsulfonyl, ethylsulfonyl, etc.), substituted and unsubstituted dialkylphosphinyl (preferably where each alkyl group independently has 1 to 10 carbon atoms, e.g. methyl, ethyl, butyl, decyl, etc.) and substituted or unsubstituted dialkyl phosphono (preferably where each alkyl group independently has 1 to 10 carbon atoms as defined above). Preferably, W is hydrogen or halo.

Y is hydrogen, or a group comprised of a heteroatom having a lone pair of electrons or a negative charge with an associated cation, e.g. hydroxy, mercapto or amino (—NR"R'"). R" and R'" are independently substituted or unsubstituted alkyl (preferably of 1 to 10 carbons, e.g., methyl, ethyl, decyl, etc.), substituted or unsubstituted aryl (preferably of 6 to 10 carbons, e.g., phenyl, naphthyl, etc.), or R" and R'", taken together, can represent the atoms necessary to complete a substituted or unsubstituted heterocyclic ring (preferably of 5 to 10 carbon, nitrogen or oxygen atoms, e.g. a morpholino, pyrrolidinyl, pyridyl, piperidino, etc. ring). Y can also be substituted or unsubstituted alkoxy (preferably of 1 to 10 carbon atoms, e.g. methoxy, ethoxy, 2-chloro-1-propoxy, etc.), substituted or unsubstituted carbamyloxy

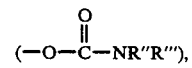

wherein R" and R'" are defined above, -O$^\ominus$ M$^\oplus$ or -S$^\ominus$ M$^\oplus$, wherein M$^\oplus$ is a monovalent cation, e.g. Na$^\oplus$, K$^\oplus$, Li$^\oplus$, NH$_4^\oplus$, etc. Preferably Y is hydroxy or -O$^\ominus$ M$^\oplus$.

Representative novel dyes of this invention are listed in Table I below in reference to the illustrated structure above. Of these, Compound 4 is preferred for use in biological studies and assays because it can be used at a pH of 7 or less. In Table I, the "fluorescence quantum efficiency" was determined by procedures described by Birks in *Standardization in Spectrophotometry and Luminescence Measurements*, Mielenz et al (Eds.), Nat. Bureau of Standards Special publication 466 (1977).

TABLE I

| Compound | R | W | Y | Emission ($\lambda_{max}$) | Fluorescence Quantum Efficiency |
|---|---|---|---|---|---|
| 1 | Methyl | Hydrogen | Hydroxy | 542 nm (in methanol) | 0.4 |
| 2 | Methyl | Hydrogen | —O$^-$Na$^+$ | 635 nm (in 5:1 water/methanol) | 0.18 |
| 3 | Methyl | Chloro | Hydroxy | 629 nm (in methanol) | 0.55 |
| 4 | Methyl | Chloro | —O$^-$Na$^+$ | 628 nm (in 5:1 water/methanol) | 0.42 |
| 5 | Methyl | Chloro | N-methyl-N-phenylcarbamyloxy | 550 nm (in 5:1 water/methanol) | 0.01 |
| 6 | Methyl | Hydrogen | Pyrrolidinyl | 655 nm (in methanol) | 0.52 |
| 7 | Butoxycarbonyl | Hydrogen | Hydroxy | 525 nm (in methanol) | 0.4 |
| 8 | Butoxycarbonyl | Hydrogen | —O$^-$Na$^+$ | 630 nm (in 5:1 water/methanol) | 0.3 |
| 9 | Butoxycarbonyl | Chloro | —O$^-$Na$^+$ | 625 nm (in 5:1 water/ |  |

TABLE I-continued

| Compound | R | W | Y | Emission ($\lambda_{max}$) (methanol) | Fluorescence Quantum Efficiency |
| --- | --- | --- | --- | --- | --- |

The compounds illustrated above can have one or more substituents other than those specifically illustrated in the structure as long as the substituents do not adversely affect the fluorescence of the compound. Such substituents include alkyl, aryl, and any other groups one skilled in the art would recognize as possible at one or more positions on the fused rings.

The novel compounds can be prepared generally using the following procedure. The details of several preparations are provided in Examples 1-4 below. The general preparatory procedure includes: (1) preparation of a dihydrophenalenone by the procedure described by Cooke et al, *Australian J. Chem.*, 11, pp. 230-235 (1958), (2) preparation of the lithium enolate of the dihydrophenalenone, (3) reaction of the lithium enolate with the appropriate phosphonium iodide reagent, and (4) reaction of this product with cupric chloride and lithium chloride to produce the chlorinated or unchlorinated dye.

Generally, the dyes described herein have limited water solubility. Therefore, when using them in an aqueous environment, it is best to first dissolve them in water miscible organic solvents, and then add the dye solution to water or buffer solutions. In some cases surfactants may be required to solubilize the dyes. Useful water miscible organic solvents and surfactants include those described below with respect to solubilization of the RIND compounds.

For biological uses, compositions of the dyes are buffered at a pH of 9 or less, preferably at a pH of 8 or less. Suitable buffers can be readily determined by one of ordinary skill in the art, and include phosphates, borates, and organic buffers as reported by Good et al in *Biochemistry* 5, 467 (1966) and *Anal. Biochem.* 104, 300 (1980).

In one embodiment, the fluorescent dyes can be used to stain biological specimens, e.g. tissues and cells, and for cell cytometry.

The fluorescent dyes of this invention can be blocked to form dye precursors. When blocked, the compounds are shiftable, as they are when attached to carriers (described below). The blocked dyes can be subjected to a suitable treatment or condition which will release the fluorescent dye from a blocking group during an assay. For example, the dye precursor can be acted upon chemically, hydrolytically or enzymatically by an analyte or other reagent.

In one embodiment, the fluorescent dye is released from a reducible compound. While attached to the reducible compound, the fluorescent dye has an emission spectrum different from the emission spectrum it exhibits when released.

More particularly, the reducible compounds of this invention have the structure CAR$(-R^1)_n$ wherein CAR- represents a substituted or unsubstituted aromatic or quinone nucleus, $R^1$ comprises a moiety derived from the fluorescent dye described above, and n is 1 or 2. Examples of CAR-nuclei are presented below. preferably, when $R^1$ is replaced by H, CAR$(-H)_n$ has a reduction potential ($e_{\frac{1}{2}}$) of at least about +100 mV when measured in water. This $E_{\frac{1}{2}}$ value facilitates the reduction and subsequent release of the dye from the compound at physiological pH (pH less than or equal to 9). Such measurements are made according to standard electrochemical techniques using either differential pulse polarography or cyclic voltametry (see, e.g. Sawyer and Roberts, Jr., *Experimental Electrochemistry for Chemists*, John Wiley & Sons, New York, 1974). Preferably, the $E_{\frac{1}{2}}$ is from about +100 mV to about +400 mV as measured in water. The desired $E_{\frac{1}{2}}$ is achieved by appropriate electron withdrawing groups on the CAR-nucleus, or by a combination of a fused ring attached to the nucleus and electron withdrawing groups.

Examples of useful reducible compounds are illustrated below without intending to limit this invention.

In one embodiment, the reducible compounds can be reduced to provide a detectable species through quinonemethide formation, similar to the description by Van de Sande in *Angew. Chem. Int. Ed. Engl.* 22, pp. 191-209 (1983) and U.S. Pat. No. 4,232,107 (issued Nov. 4, 1980 to Janssens), but which have the desired $E_{\frac{1}{2}}$ properties.

In another embodiment, useful reducible compounds include sulfilimides and sulfenylsulfonamides similar to those described on page 206 of the Van de Sande reference noted above, but which have the desired $E_{\frac{1}{2}}$ properties.

In a preferred embodiment, the reducible compounds are RIND compounds, i.e. reducible compounds capable of undergoing intramolecular nucleophilic displacement, preferably at physiological pH, to release one or more fluorescent dyes when a nucleophilic group is generated by at least electron reduction of the compound. In other words, such displacement occurs when the RIND compound is reduced by a suitable reductant.

The term "intramolecular nucleophilic displacement" refers to a reaction in which a nucleophilic center on a molecule reacts at another site in the molecule, which site is an electrophilic center, to effect displacement of a group or atom attached to the electrophilic center. Generally, the RIND compounds of this invention have the nucleophilic and electrophilic groups juxtaposed in the three-dimensional configuration of the molecule in close proximity whereby the intramolecular reaction can take place and a ring is formed having from 4 to 7, and preferably 5 or 6, atoms. The rate of nucleophilic displacement is substantially zero prior to reduction of the RIND compound.

Particularly useful RIND compounds are those which have the structure CAR-$R^1$ wherein CAR- is

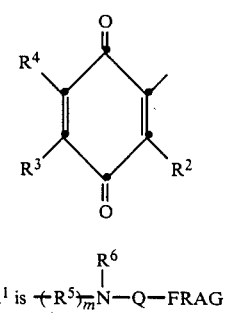

$R^1$ is $(R^5)_m$N—Q—FRAG wherein m is 0 or 1, and preferably 1. $R^5$ is substituted or unsubstituted alkylene, preferably of 1 or 2 carbon atoms in the backbone (e.g. methylene, ethylene, alkoxymethylene, etc.). Most preferably, $R^5$ is methylene. Q is carbonyl or thiocarbonyl and preferably carbonyl.

$R^6$ is substituted or unsubstituted alkyl preferably of 1 to 40 carbon atoms (e.g. methyl, ethyl, n-propyl, isopropyl, t-butyl, hexyl, decyl, lauryl, benzyl, etc.), substituted or unsubstituted cycloalkyl preferably of 4 to 40 carbon atoms (e.g. obutyl, cyclohexyl, 4-methylcyclohexyl, etc.), substituted or unsubstituted heterocycle preferably of 5 to 20 carbon and heteroatoms (e.g. pyridyl, etc.), or substituted or unsubstituted aryl of 6 to 40 carbon atoms (e.g. phenyl, xylyl, naphthyl, p-nitrophenyl, anthryl, p-t-butoxyphenyl, etc.). Preferably, $R_6$ is unsubstituted lower straight chain alkyl of 1 to 6 carbon atoms (e.g. methyl, ethyl, n-propyl, n-butyl, n-hexyl, etc.), most preferably, $R^6$ is methyl.

FRAG is a fluorescent moiety derived from a 4-oxo-4H-benz-[d,e]anthracene of this invention described above wherein Y is hydroxy or mercapto. Preferably, Y is hydroxy. FRAG is attached to the carrier nucleus through the Y group. The dye is released from the rest of the molecule in an amount directly proportional to the amount of reductant present.

$R^2$, $R^3$ and $R^4$ in the above quinone structure are independently hydrogen, substituted or unsubstituted alkyl of 1 to 40 carbon atoms (e.g. methyl, ethyl, hydroxymethyl, methoxymethyl, benzyl, etc.) substituted or unsubstituted aryl (e.g. phenyl, naphthyl, methylnaphthyl, p-nitrophenyl, m-methoxyphenyl, phenylsulfonamido, etc.) or an electron withdrawing group which generally has a positive Hammett sigma value, and preferably has a sigma value greater than about 0.06. Hammett sigma values are calculated in accordance with standard procedures described, e.g. in *Steric Effects in Organic Chemistry*, John Wiley & Sons, Inc., 1956, pp. 570–574 and *Progress in Physical Organic Chemistry*, Vol. 2, Interscience Publishers, 1964, pp. 333–339. Representative useful electron withdrawing groups having positive Hammett sigma values include cyano, carboxy, nitro, halo (e.g. fluoro, bromo, chloro, iodo), trihalomethyl (e.g. trifluoromethyl, trichloromethyl, etc.), trialkylammonium, carbonyl, carbamoyl, sulfonyl, sulfamoyl, esters and others known in the art, or alkyl or aryl groups (defined above) substituted with one or more of these electron withdrawing groups. Preferred electron withdrawing groups include p-nitrophenyl, m-nitrophenyl, p-cyanophenyl and 2,5-dichlorophenyl. Aryl groups with methoxy or acetamido groups in the meta position are also useful.

$R^3$ can also be $R^1$ thereby potentially providing a 2:1 molar ratio of fluorescent dye molecules to original RIND compound molecules.

Alternatively, $R^3$ and $R^4$, taken together, can represent the carbon atoms necessary to complete a substituted or unsubstituted fused carbocyclic ring attached to the quinone nucleus. For example, such a ring (mono- or bicyclic) can have from 4 to 8, and preferably from 5 to 7, carbon atoms in the backbone.

The RIND compounds useful in this invention are prepared using a sequence of individually known reactions. Generally, the preparation sequence includes the following general steps: (1) preparation of the substituted hydroquinone, (2) oxazine ring formation, (3) oxazine ring opening, (4) preparation of the carbamoyl chloride, and (5) reaction of the FRAG moiety with the carbamoyl chloride. Representative preparations of RIND compounds are provided in U.S. Ser. No. 824,766 now U.S. Pat. 4,857,271 of Belly et al noted above, as well as in copending and commonly assigned U.S. Ser. No. 824,757 now U.S. Pat. No. 4,803,161 of Babb et al, entitled BIOLOGICAL AND ANALYTICAL USES OF PHENALENONE AND BENZPHENALENONE COMPOUNDS filed on even date herewith.

Other RIND compounds useful in the practice of this invention include those having the appropriate $E_{\frac{1}{2}}$ values and the structure CAR-($-R^1$)$_n$ wherein:

(1) CAR is a substituted or unsubstituted nucleus of a 1,2-naphthoquinone, 1,2-, 1,4- or 9,10-anthraquinone, 4,4'-diphenoquinone, azuloquinone or 1,6-[10]-anulenoquinone wherein $R^1$ is attached to the nucleus one carbon atom distant or in the peri position from one of the oxo groups of the nucleus. The nucleus can be substituted with one or more electron withdrawing groups as described above for $R^2$ or have one or more fused rings as described above for $R^3$ and $R^4$. $R^1$ is

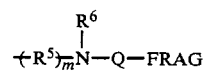

as defined above, and n is an integer of 1 or 2.

(2) CAR- is 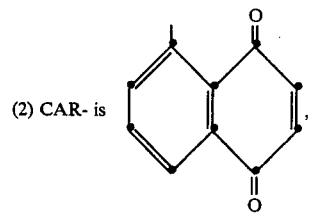

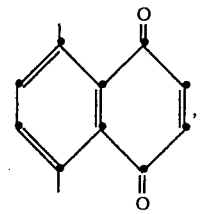

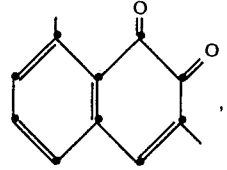

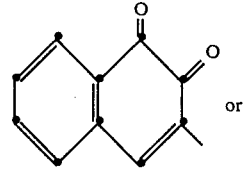 or

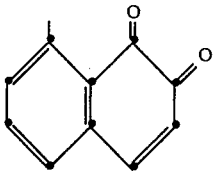

any of which can be substituted with one or more electron withdrawing groups as described above for $R^2$, $R^3$ and $R^4$. R1 is

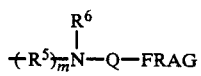

as defined above, and n is 1 or 2.

(3) CAR is a substituted or unsubstituted nitrobenzenoid nucleus of the structure

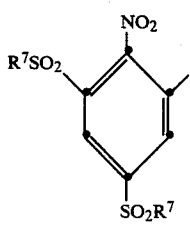

wherein $R^7$ is substituted or unsubstituted alkyl of 1 to 20 carbon atoms (e.g. methyl, ethyl, methoxymethyl, isopropyl, dodecyl, hexadecyl, octadecyl, etc.), and $R^1$ is

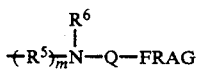

as defined above and n is 1. These compounds are similar to some described in U.S. Pat. No. 4,139,379 (issued Feb. 13, 1979 to Chasman et al).

All of these reducible compounds can be prepared using techniques and starting materials known in the art or readily apparent to a skilled synthetic chemist.

Generally, the reducible compounds described herein have limited water solubility. Hence, it is best, when using them in an aqueous environment, to prepare a dispersion of the compound prior to use, e.g. in a coating formulation. Such dispersions generally comprise the reducible compound, an aqueous buffer solution and either a surfactant or a water-miscible organic solvent for the compound, or both.

Surfactants which are useful in the practice of this invention include any surfactants which do not inhibit compound reduction. Generally, for detection of living cells, the useful surfactants are nonionic surfactants, including, for example, alkylarylpolyethoxy alcohols (e.g. TRITON X-100 and X-305 available from Rohm & Haas, Philadelphia, Pa., U.S.A.), p-alkylaryloxypolyglycidols (e.g. SURFACTANT 10G available from Olin Corp., Stamford, Conn., U.S.A.), TWEEN 80 (available from ICI Americas, Inc., Wilmington, Del., U.S.A.), and others known to one skilled in the art.

Useful water miscible organic solvents include alcohols (e.g. methanol, ethanol, propanol, etc.), N,N-dimethylformamide, dimethyl sulfoxide, acetonitrile, hexamethylenephosphoramide and the like. The particular solvent to be used for a particular reducible compound can be readily determined by routine experimentation.

A dispersion can be prepared in the following general manner. The reducible compound is dissolved in the water-miscible solvent at a concentration which depends upon its molecular weight, but generally at from about 1 to about 100, and preferably from about 5 to about 80, mg per ml of solvent. The resulting solution is then mixed with a suitable surfactant in an amount generally of from about 0.1 to about 24, and preferably from about 0.5 to about 10, mg surfactant per ml of dispersion. This preparation is generally carried out at room temperature.

These dispersions preferably contain a buffer in an amount effective to maintain a physiological pH (9 or less). The concentration of buffer in the dispersion can vary widely, but is generally from about 0.01 to about 0.1 molar. Representative buffers are described above.

The reducible compounds described herein are useful in compositions for analytical determination (i.e. qualitative or quantitative detection) of aqueous and nonaqueous liquids, e.g. biological fluids, manufacturing processes, wastewater, food stuffs, etc. Determinations can be made of various analytes, including living cells (e.g. bacteria, yeast, fungi, etc.), enzymes (e.g. lipase, glucose oxidase, lactate oxidase, creatine kinase, $\alpha$-glycerophosphate oxidase, lactate dehydrogenase, alanine aminotransferase, aspartate aminotransferase and other NADH-based, FADH-based or peroxidase based assays which include dehydrogenase or reductase enzymes), biological or chemical reductants other than living cells which will reduce the reducible compound (e.g. ascorbates, cysteine, glutathione, thioredoxin, etc.), metabolizable substances (e.g. glucose, lactic acid, triglycerides, cholesterol, etc.), immunoreactants (e.g. antigens, antibodies, haptens, etc.), and other determinations made via a single reaction or sequence of reactions which brings about reduction of the compound and release of the fluorescent moiety. The reducible compound can be used in combination with an interactive composition which is capable of reacting with an analyte to provide an oxidant which will reduce the reducible compound.

The reducible compounds described herein are particularly useful in detecting or quantifying living cells in biological samples. Although any biological sample suspected of having living cells therein (e.g. food, tissue, ground water, cooling water, pharmaceutical products, sewage, etc.) can be analyzed for bacteria, yeast, fungi, etc. by this invention, it is particularly useful for bacterial detection in aqueous liquids, such as human and animal fluids (e.g. urine, cerebral spinal fluid, blood and the life as well as stool secretions) and suspensions of human or animal tissue. The practice of this invention is particularly important for detection of urinary tract infections in urine (diluted or undiluted).

When determining living cells using the reducible compounds, it is preferable for rapid dye release that the living cells interact with an electron transfer agent (herein ETA). The presence of an ETA may provide more efficient dye release for analytical determinations of nonliving analytes. The ETA is a mobile compound which acts as an intermediary between the substance being determined (e.g. living cell) and the reducible compound. In general, the ETA compounds are present at a concentration that is dependant upon the concentration of the analyte, but preferably at a concentration of from about $1 \times 10^{-3}$ molar to about $1 \times 10^{-7}$ molar.

Useful ETA compounds include phenazine methosulfate, phenazine ethosulfate and similar compounds known to one skilled in the art. Combinations of different ETA compounds can be used if desired. Preferred ETA compounds which provide further advantages of low background are those which are the subject of U.S. Ser. No. 699,374 filed Feb. 7, 1985 by Mura et al. In general, those compounds are substituted benzo- and naphthoquinones. Examples of this class of quinones include 2,3-dimethyl-5-hydroxymethyl-1,4-benzoquinone, 2,5-dimethoxy-1,4-benzoquinone, 2,3,5-trimethyl-1,4-benzoquinone, 2,6-dimethoxy-1,4-benzoquinone, 2-hydroxymethyl-1,4-naphthoquinone and 2-(2-hydroxyethyl)-1,4-naphthoquinone.

The detection of living cells, and particularly of bacterial cells, is often carried out in the presence of a nutrient for those cells although its presence is not essential. Any nutrient medium can be used which contains useful carbon, and optionally nitrogen, sources. Suitable nutrient media having proper components and pH are well known in the art. Particularly useful nutrients are glucose or tryptose alone or in combination.

The present invention can also be used for the determination of hydrolytic analytes (living or nonliving). As used herein the term "hydrolytic analyte" refers to a substance (chemical substance, enzyme or organism) which is capable of hydrolyzing the hydrolyzable compound of this invention (defined below) by cleaving the BLOCK group from the remainder of the molecule, preferably at a pH of 9 or less. This invention is particularly useful for determining hydrolytic enzymes, such as esterases, amidases, proteases, and microorganisms or cells containing those enzymes, such as *Nissera spp.*, including those enzymes and organisms listed in WO patent application No. 80/02433 (published Nov. 13, 1980). The hydrolyzable compound can be designed with the appropriate BLOCK group and linkage to determine a particular analyte. For example, the invention can be used to identify *Enterobacter cloacae* or *Klebsiella pneumoniae* when BLOCK is derived from a monosaccharide moiety, L is hydrogen and X is oxy. Hydrolytic analytes can be determined in biological fluids, e.g. urine, cerebral spinal fluid, blood, lymph fluids, tissue homogenate, mucous, saliva, stool secretions, etc. using the hydrolyzable compounds of this invention as substrates.

These substrates are represented by the formula:

BLOCK-X-R$f$-L.

In this formula, BLOCK represents any hydrolyzable blocking group which can be cleaved from the remainder of the molecule, preferably at a pH of 9 or less. Generally, the blocking group is chosen based on the analyte specificity desired. Representative blocking groups include, for example, -COR*, phosphono or thioxophosphono or a salt thereof or a moiety derived from an amino acid, peptide or mono- or polysaccharide. Preferably, BLOCK is -COR*.

R* can be hydrogen, substituted or unsubstituted alkyl (preferably of 1 to 20 carbon atoms, e.g. methyl, ethyl, chloroethyl, isopropyl, benzyl, chlorobenzyl, etc.), substituted or unsubstituted alkenyl (preferably of 2 to 20 carbon atoms, e.g. ethenyl, 2 propenyl, 4-hexenyl, etc.), substituted or unsubstituted aryl (preferably of 6 to 12 carbon atoms, e.g. phenyl, methoxyphenyl, etc.), substituted or unsubstituted cycloalkyl (preferably of 5 to 12 carbon atoms, e.g. cyclopentyl, cyclohexyl, etc.), or a substituted or unsubstituted heterocyclic group (preferably of 6 to 12 carbon, sulfur, nitrogen and oxygen atoms, e.g. pyridyl, thienyl, etc.).

The X group of the formula above is oxy, thio or imino (—NR'—, wherein R' is hydrogen or substituted or unsubstituted alkyl of 1 to 10 carbon atoms, e.g. methyl, ethyl, propyl, isopropyl, decyl, benzyl, etc., substituted or unsubstituted cyclohexyl, substituted or unsubstituted phenyl or a substituted or unsubstituted heterocyclic group as defined above, e.g. pyridyl, thienyl, etc.). Preferably, X is oxy or imino wherein R' is hydrogen or lower alkyl of 1 to 3 carbon atoms.

R$f$ is a moiety derived from the fluorescent dyes of this invention. When BLOCK is cleaved from the remainder of the molecule by hydrolysis, the resulting hydrolyzed moiety (i.e. -X-R$f$-L) can preferably be detected at a pH of less than 9 in an aqueous environment. Most preferably, the hydrolyzed moieties can be detected at a pH of less than 8.

In the formula shown above, L is preferably hydrogen. However, L can also be a specific binding ligand so that the substrate can be used in a substrate-label fluorescent immunoassay as described, for example, in U.S. Pat. No. 4,279,992 (issued July 21, 1981 to Boguslaski et al). In such assays, the analyte to be determined is a ligand which will complex with a specific receptor. The assay is based on using a label that is a fluorogenic enzyme substrate. When the label is hydrolyzed by a specific enzyme, it yields a fluorescent dye. Binding of the labeled ligand by the receptor prevents the enzyme from hydroylzing the substrate. Since a fluorescent dye will not be produced by antibody-bound label, bound label can be distinguished from unbound label.

The assay can be used for the determination of any specific binding ligand, particularly haptens, such as drugs, and antibodies, antigens, hormones, polypeptides, etc. The substrates can also be used in what are known in the art as "sandwich" assays.

When L is a specific binding ligand, it is attached to R$f$ by a covalent linking group. It will be recognized that there are many methods for covalently linking the ligand to R$f$. The particular chemical character of the linking group will depend upon the nature of the respective available the linking sites on the ligand and R$f$. Selection of the linking group depends upon preservation of the ability of the ligand to participate in the specific binding reaction and the retention of desired pKa, absorption and emission properties. Generally, the linking group comprises a single or a double bond, or a chain containing between 1 and 10 carbon or heteroatoms in the chain. Particular examples of useful linking groups and methods of preparing -R$f$-L are described in U.S. Pat. No. 4,279,992 noted above.

Depending upon their water solubilities, the substrates of this invention can be either dissolved directly in buffers or in a combination of buffer and water-miscible organic solvents, or dispersions can be prepared containing a substrate, buffer, water-miscible organic solvent and surfactant.

When used for the determination of enzymes or organisms, the solution is buffered at 9 or less with one or more appropriate buffers. Useful buffers are readily determined by one skilled in the art and include phosphates, borates and organic buffers as reported by Good et al in *Biochem.* 5, 467 (1966) and *Anal. Biochem.* 104, 300 (1980). Preferably the solution is buffered to a pH of 8 or less.

Surfactants which are useful in the practice of this invention include any surfactants which do not inhibit compound hydrolysis. Generally, for detection of living cells, the useful surfactants are nonionic surfactants, including, for example, those noted above.

Useful water miscible organic solvents include alcohols (e.g. methanol, ethanol, propanol, etc.), N,N-dimethylformamide, dimethyl sulfoxide, acetonitrile, hexamethylenephosphoramide and the like. The particular solvent to be used for a particular substrate can be readily determined by routine experimentation.

A solution of the substrate can be prepared in the following general manner. The substrate is dissolved in the water-miscible solvent at a concentration which depends upon its molecular weight, but generally at from about 1 to about 100, and preferably from about 5 to about 80, mg per ml of solvent. The resulting solution is then mixed with a suitable surfactant in an amount generally of from about 0.1 to about 24, and preferably from about 0.5 to about 10, mg surfactant per ml of solution. This preparation is generally carried out at room temperature.

These solutions generally contain a buffer in an amount effective to maintain a physiological pH (9 or less). The concentration of buffer in the dispersion can vary widely, but is generally from about 0.01 to about 0.5 molar. Representative buffers are described above.

The determination of hydrolytic analytes, and particularly of bacterial cells, is often carried out in the presence of a nutrient for those cells although its presence is not essential. Any nutrient medium can be used which contains useful carbon, and optionally nitrogen, sources. Representative nutrients are noted above.

Some enzyme analytes require an inducer, i.e. a material or a combination of materials that promote the formation of the enzyme in the cell. The type of inducer or induction medium used is dependent upon the enzyme to be formed and determined. In some cases, both an inducer and a nutrient may be needed to promote formation. Another method of induction is to incubate the substrate in the presence of the nutrient for several minutes at appropriate temperatures prior to testing for the analyte.

The present invention is adaptable to either solution or dry assays. In a solution assay, a solution (or aqueous dispersion) containing either a reducible compound or a hydrolyzable compound, can be prepared and contacted with a liquid test sample containing the living cells or analyte to be determined by mixing. An ETA can also be mixed with the test sample prior to mixing with a reducible compound. Generally either the reducible compound or hydrolyzable compound is mixed with the test sample in a suitable container (e.g. test tube, petri dish beaker, cuvette, test device, etc.). The resulting solution (or dispersion) is gently mixed and incubated for a relatively short time (i.e. up to about 30 minutes) at a temperature up to about 40° C., and generally from about 20° to about 40° C. The test sample is then evaluated by measuring the resulting fluorescent dye with suitable detection equipment.

A solution assay can also be carried out by contacting a porous, absorbent material, e.g. paper strip, containing the test sample with a dispersion of the reducible compound or hydrolyzable compound. The analyte in the test sample can migrate from the porous material into the dispersion and initiate the analytical reactions needed for determination. In solution assays, the amount of reducible compound present is at least about 0.001, and preferably from about 0.01 to about 1.0, millimolar. Where a hydrolyzable compound oF this invention is used, it is generally present in an amount of at least about 0.01, and preferably from about 10 to about 100, millimolar. Other reagents can be present in amounts readily determined by one skilled in the art.

Alternatively, the method of this invention can be practiced with a dry analytical element. Such an element can be an absorbent carrier material, i.e. a thin sheet or strip of self-supporting absorbent or bibulous material, such as filter paper or strips, which contains the reducible compound or hydrolyzable compound or a dried residue of the dispersion comprising same. Such elements are known in the art as test strips, diagnostic elements, dip sticks, diagnostic agents and the like.

When employed in dry analytical elements, the compounds described herein can be incorporated into a suitable absorbent carrier material by imbibition or impregnation, or can be coated on a suitable absorbent carrier material. Alternatively, they can be incorporated in the element during an assay. Useful carrier materials are insoluble and maintain their structural integrity when contacted with water or physiological fluids such as urine or serum. Useful carrier materials can be prepared from paper, porous particulate structures, cellulose, porous polymeric films, wood, glass fiber, woven and nonwoven fabrics (synthetic and non-synthetic) and the like. Useful materials and procedures for making such elements are well known in the art as exemplified by U.S. Pat. Nos. 3,092,465 (issued June 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,8Z9 (issued Feb. 3, 1981 to Kitajima et al), 4,255,384 (issued Mar. 10, 1981 Kitajima et al), and 4,270,920 (issued June 2, 1981 to Kondo et al), and U.K. Patent No. 2,052,057 (published Jan. 21, 1981).

A dry assay can be practiced to particular advantage with an analytical element comprising a support having thereon at least one porous spreading zone as the absorbent carrier material. The reducible or hydrolyzable compound can be in the spreading zone or in a different zone (e.g. reagent zone, registration zone, hydrophilic zone, etc.).

The spreading zone can be prepared from any suitable fibrous or non fibrous material or mixtures of either or both as described in U.S. Pat. No. 4,292,272 (issued Sept. 29, 1981 to Kitajima et al), polymeric compositions (e.g. blush polymers) or particulate materials, with or without binding adhesives, as described in U.S. Pat. Nos. 3,992,158 (issued Nov. 16, 1976 to przybylowicz et al), 4,258,001 (issued Mar. 24, 1981 to pierce et al) and 4,430,436 (issued Feb. 7, 1984 to Koyama et al) and Japanese Patent Publication 57(1982)-101760 (published June 24, 1982). It is desired that the spreading zones be isotropically porous, meaning that the porosity is the same in each direction in the zone as created by interconnected spaces or pores between particles, fibers, polymeric strands, etc.

The dry analytical element of this invention can be a single self supporting absorbent carrier material containing desired reagents for a particular assay, but preferably such material is carried on a suitable nonporous support. Such a support can be any suitable dimensionally stable, and preferably, transparent (i.e. radiation transmissive) film or sheet material which transmits electromagnetic radiation of a wavelength between about 200 and about 900 nm. A support of choice for a particular element should be compatible with the intended mode of detection and inert to chemical reagents and liquid samples used in the assay. Useful support materials include polystyrene, polyesters [e.g. poly(ethylene terephthalate)], polycarbonates, cellulose esters (e.g. cellulose acetate), etc.

The elements can have more than one zone, e.g. a reagent zone, a registration zone, subbing zone, etc. The zones are generally in fluid contact with each other, meaning that fluids, reagents and reaction products can pass between superposed regions of adjacent zones. Preferably, the zones are separately coated superposed layers, although two or more zones can be located in a single coated layer. Besides the przybylowicz et al and pierce et al patents noted above, suitable element formats and components are described also, for example, in U.S. Pat. Nos. 4,042,335 (issued Aug. 16, 1977 to Clément) and 4,144,306 (noted above) and Reissue 30,267 (reissued May 6, 1980 to Bruschi).

In the elements of this invention, the amount of the reducible compound can be varied widely, but is generally present in a coverage of at least about 0.01, and preferably from about 0.05 to about 0.2, $g/m^2$. A hydrolyzable substrate is generally used in an amount of at least about 0.01, and preferably from about 0.05 to about 1, $g/m^2$. Optional, but preferred reagents (e.g. ETA, nutrient, buffer, etc.) are generally present in the following coverages:

ETA: generally at least about 0.001, and preferably from about 0.01 to about 1, $g/m^2$, nutrient: generally at least about 0.05, and preferably from about 0.1 to about 2, $g/m^2$ (used only in living cell detection), buffer (pH≦9): generally at least about 0.1, and preferably from about 0.5 to about 2, $g/m^2$, and surfactant: generally at least about 0.1, and preferably from about 0.2 to about 5, $g/m^2$.

inducer: generally at least about 0.01 $g/m^2$.

One or more of the zones can contain a variety of other desirable, but optional, components, including activators, binders (generally hydrophilic), antioxidants, coupler solvents, etc. as is known in the art, as well as any reagents needed for assay of a particular analyte.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, an analyte determination is made by taking the element from a supply roll, chip pack et or other source and contacting it with a sample (e.g. 1–200 μl) of the liquid to be tested so that the sample mixes with the reagents in the element. Such contact can be accomplished in any suitable manner, e.g. dipping or immersing the element into the sample or, preferably, by spotting the element by hand or machine with one or more drops of the sample with a suitable dispensing means.

After sample application, the element is exposed to any conditioning, such as incubation, heating or the like, that may be desirable to quicken or otherwise facilitate obtaining any test result.

Generally, when the hydrolyzable substrate of this invention is used to determine a hydrolytic analyte, the assay (solution or dry) is carried out under conditions that promote hydrolysis of the substrate by the hydrolytic enzyme. Such hydrolyzing conditions include conditions of pH and temperature which are conducive to hydrolysis. Generally, the pH will vary from one analyte to another but be less than 9, and preferably less than 8. The temperature is not critical but is generally up to about 50° C.

Detection of an analyte (nonliving or living) is achieved when a reducible compound is reduced as a result of the presence of the analyte, releasing a fluorescent dye which can be detected in a suitable manner. Alternatively, a hydrolyzable compound is hydrolyzed as a result of the presence of a hydrolytic analyte, releasing a fluorescent dye which can be detected in a suitable manner. Determinations can be made at the maximum wavelength, or they can be made at other wavelengths. Determination can be either a rate determination or an end point determination. The time of reaction can vary from analyte to analyte and can be readily chosen by a skilled clinical chemist.

In the examples which follow illustrating the practice of the invention, the materials used were obtained as follows:

TRITON X-100 nonionic surfactant from Rohm and Haas (Philadelphia, Pa., U.S.A.), brain heart infusion medium from Difco Labs (Detroit, Mich., U.S.A.), E. coli cells and carboxyl esterase, Type I and HEpES (N-2-hydroxyethylpiperazine-N'-2-ethanesulfonic acid) buffer from Sigma Chemical Co. (St. Louis, Mo., U.S.A.), and the remainder from Eastman Kodak Co. (Rochester, N.Y., U.S.A.), or prepared using readily available or prepared starting materials using known techniques.

EXAMPLE 1:

Preparation of Fluorescent Compound 1 n-Butyllithium (7 mmole in 3.5 ml of hexane) was slowly added to a well stirred, cold (−70° C.) solution of diisopropylamine (1 ml, 7.2 mmole) in dry tetrahydrofuran under argon atmosphere. After stirring for five minutes, a solution of 1.5 g, 7.0 mmole of 6-methoxydihydrophenalenone in 20 ml of tetrahydrofuran was slowly added.

The resulting dark-colored solution was stirred at −70° C. for 1.5 hours. The solution was then transferred using a syringe, to a round bottomed flask containing 5 g (10 mmole) of (2-ethoxy-1,3-pentadienyl)triphenylphosphonium iodide prepared according to the procedure described by Martin et al in *J Org. Chem.* 43, pp.4673–4676 (1978). The resulting suspension was stirred at room temperature for 1 hour and refluxed for 3 hours. All of the steps were carried out under argon and the exclusion of moisture.

The suspension was then cooled to room temperature, 50 ml of 1 normal hydrochloric acid added and stirred vigorously for 1 hour. Then 50 ml of ether were added and the layers separated. Three additional ether extractions were combined with the first and the ether solution was washed in turn with saturated sodium bicarbonate solution, water, and saturated sodium chloride solution. The ether solution was dried and the solvent evaporated to yield about 3 g of solid residue. The residue was purified via flash chromatography on silica gel using a 10:45:45 ethyl acetate, dichloromethane, cyclohexane mixture as the eluent. The desired product was seen as an orange band when illuminated with a long wavelength (355 nm) ultraviolet lamp. The bands containing the orange fluorescent dye were combined, the solvents evaporated yielding 860 mg (44% yield) of 4-methoxy-8-methyl-10-oxo-7,8,9,10-tetrahydrobenzo[d,e]anthracene having a m.p. of 135°–136° C. and m/e of 278(M+). *The calculated analysis for* $C_{19}H_{18}O$ *was* C, 82.0 H, 6.2 with the found of C, 81.7, H, 6.3.

A solution of 530 mg (1.9 mmole) of the compound identified above, in N,N-dimethylformamide (15 ml), was slowly added to a solution of 700 mg (4.1 mmole) of cupric chloride hydrate and 200 mg (4.7 mmole) of lithium chloride in N,N-dimethylformamide (30 ml) heated to 90° C. The resulting mixture was stirred for 70 minutes. Ice was added to the mixture and the resulting brown solid was separated and washed several times with cold water, yielding 397 mg (80% yield) of Dye 1. This product was shown to be pure by thin layer chromatography on silica gel, but was recrystallized from ethyl acetate-ethanol to give a material with a m.p. of 289°–295° C., and m/e of 260($M^+$). The structure of the dye was confirmed by the analysis of its N-phenyl-N-methylcarbamate derivative. The calculated analysis for $C_{26}H_{19}NO_3$ was C, 79.4, H, 4.9, N, 3.6 and found was C, 79.2, H, 5.1, N, 3.8.

EXAMPLE 2:

Preparation of Fluorescent Dye 3

Cupric chloride dihydrate (2.45 g, 14.4 mmole) and lithium chloride (1.0 g, 22.7 mmole) were suspended in 20 ml of N,N-dimethylformamide (DMF) heated to 90° C. To this hot mixture was added a solution of 650 mg, (2.34 mmole) of the methoxy ketone intermediate of Example 1 dissolved in 10 ml of DMF. The mixture was kept at 90° C. for 24 hours and then quenched by adding ice and water. The resulting precipitate was washed several times with water and dried. It was purified by triturating with 10% methanol in 1:1 ethyl acetate/dichloromethane, yielding 300 mg (44%) of Dye 3. The product from the trituration step is pure enough for the intended applications. It can be further purified by flash chromatography on silica gel using 20% ethyl acetate in a 1:1 dichloromethane/cyclohexane mixture as eluent, yielding material with m.p. of 238°–240° C. The structure of Dye 3 was confirmed by the elemental analysis of both its methyl ether and its N-phenyl-N-methylcarbamate derivatives.

Analysis for methyl ether derivative $C_{19}H_{13}ClO_2$: Calcd: C, 73.9, H, 4.2. Found: C, 74.0, H, 4.1.

Analysis for carbamate derivative $C_{26}H_{18}ClNO_3$: Calcd: C, 73.0, H, 4.2, N, 3.3. Found: C, 72.8, H, 4.1, N, 3.1.

EXAMPLE 3:

Preparation of Fluorescent Dye 5

N-phenyl-N-methylcarbamoyl chloride (1.2 equivalents) was added to a mixture of 1.2 equivalents each of pyridine and Dye 3 of Example 2 in toluene as solvent and the mixture heated to reflux for 12 hours. The toluene solution was cooled, washed with dilute hydrochloric acid, then water, and finally brine. The organic phase was separated and the solvent evaporated. The residue was purified by flash chromatography on silica gel using 20% ethyl acetate in 1:1 dichloromethane/cyclohexane as the eluent. Dye 5 has m.p. of 233°–235° C. and the elemental analysis given for the carbamate in Example 2.

EXAMPLE 4:

Preparation of Fluorescent Dye 6

The methoxy ketone intermediate of Example 1 (400 mg, 1.4 mmole) dissolved in a small amount of dichloromethane was added to 5 ml, 59.8 mmole of pyrrolidine in 100 ml of anhydrous methanol and the mixture refluxed for four days with stirring. The mixture was cooled and the solvents evaporated under reduced pressure. The residue was purified by flash chromatography on silica gel using 1:1 dichloromethane/cyclohexane containing ethyl acetate ranging from 0% at the start to 50% at the end of the reaction. The appropriate fractions were combined and the solvents evaporated. The residue was triturated with ethyl acetate and filtered, giving Dye 6 in 44% yield, with m.p. of 244°–246° C., m/e 313 of (M+).

EXAMPLE 5:

Preparation and Analytical Use of Reducible Compound

This example illustrates the use of a RIND compound of this invention for the determination of E. coli cells. The RIND compound used is represented by the structure:

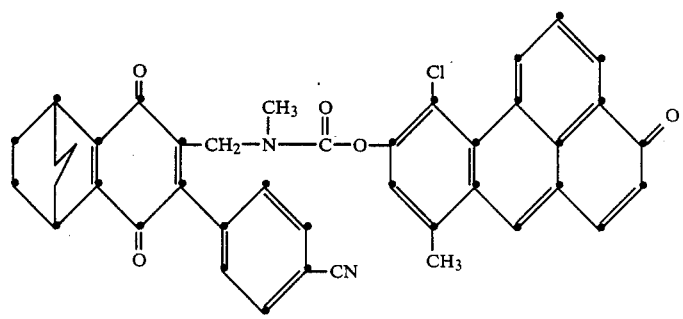

This compound was prepared according to the procedures described above.

A dispersion of the RIND compound was prepared by dissolving it (4.7 g) in dimethyl sulfoxide (DMSO, 500 μl) which had been acidified with concentrated sulfuric acid (10 μl per ml of DMSO). The RIND solution was added to 500 μl of TRITON X-100 nonionic surfactant, and the resulting solution was added dropwise with stirring to HEpES buffer (25 ml, pH 7.8) to form a RIND dispersion. E. coli cells (ATCC 25922) used in this example were grown in brain heart infusion medium at 37° C. without shaking and transferred daily.

A test solution was prepared from the following: HEPES buffer (1.5 ml), RIND dispersion (1.5 ml), 10% glucose solution (25 μl), trimethylbenzoquinone electron transfer agent (25 μl of a solution of 4.5 mg/3 ml of methanol) and E. coli cells (60 μl having $1 \times 10^7$ cells/ml). A Control solution was similarly prepared but omitting the E. coli cells.

The fluorescence of the dye released in the test solution as a result of the reduction of the RIND compound by the cells was measured by excitation at 540 nm and emission at 610 nm with a commercially available fluorometer when first adding the cells and after 30 minutes.

The fluorescence of the Control solution was similarly measured. The results are shown in Table II below in terms of the change (Δ) in relative fluorescence after 30 minutes.

TABLE II

| Test Solution | Δ Relative Fluorescence After 30 Minutes |
|---|---|
| Control | 0.014 |
| Example 5 | 0.125 |

EXAMPLE 6:

Prepration and Analytical Use of Hydrolyzable Compound

This example demonstrates that a hydrolyzable compound of this invention can be used to determine an esterase enzyme. The hydrolyzable compound used is represented by the structure:

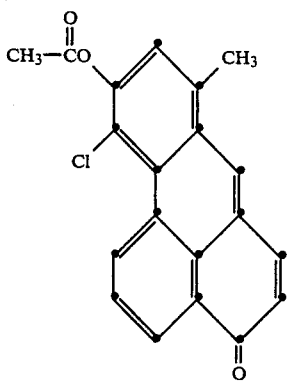

This hydrolyzable substrate was prepared in the following manner: the corresponding hydroxy compound (200 mg) was dissolved in pyridine (20 ml), and then acetic anhydride (5 ml) was slowly added. The resulting reaction mixture was stirred at about 25° C. for 16 hours, and poured with stirring into ice and dilute hydrochloric acid. The product was collected by filtration and washed with water. Thin layer chromatography (silica, 20% acetone in pentane) showed the presence of a new compound. This product was dissolved in a mixture of methylene chloride, ethyl acetate and acetone and purified by flask chromatography (silica, 20% acetone in pentane). Nuclear magnetic resonance was used to confirm the structure.

A test solution was prepared from the following: the hydrolyzable substrate (50 μl of a solution of 0.1 mg/0.5 ml of methanol), 0.05 molar HEPES buffer (3 μl, pH 7.8) and the esterase enzyme carboxyl esterase, Type I (50 μl). A Control solution was similarly prepared by omitting the enzyme. Fluorescence of the released fluorescent dye was measured with a commercially available fluorometer when the enzyme was first added to the test solution and at various times thereafter (excitation at 540 nm and emission at 610 nm). The Control solution was similarly evaluated at the indicated times. The resulting data, provided in Table III below, indicates that the hydrolyzable substrate of this invention is useful for determination of a hydrolytic analyte.

TABLE III

| Test Solution | Final Enzyme Activity (I.U.) | Δ Relative Fluorescence (Minutes) | | | |
|---|---|---|---|---|---|
| | | 0 | 1 | 2 | 5 |
| Control | 0 | 1.8 | 1.8 | 1.8 | 1.8 |
| Example 6 | 48 | 8.1 | 31.5 | 32.1 | 33.3 |

As used in the context of this disclosure and the claims, I.U. represents the International Unit for enzyme activity defined as one I.U. being the amount of enzyme activity required to catalyze the conversion of 1 micromole of substrate per minute under standard pH and temperature conditions for the enzyme.

The invention has been described in detail with particular reference to preferred embodiments thereof, but it will be understood that variations and modifications can be effected within the spirit and scope of the invention.

We claim:

1. A substituted or unsubstituted 4-oxo-4H-benz-[d,e]anthracene.

2. The compound of claim 1 represented by the structure

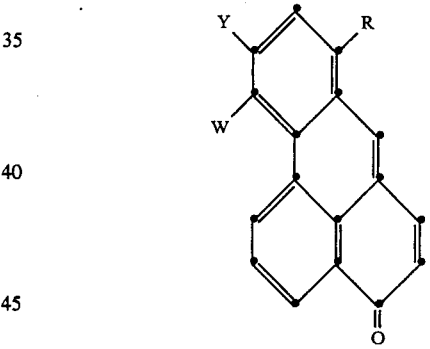

wherein R is hydrogen, substituted or unsubstituted alkyl, substituted or unsubstituted hydroxyalkyl or substituted or unsubstituted alkoxycarbonyl, W is hydrogen or an electron withdrawing group, and Y is hydrogen or a group comprised of a heteroatom having a lone pair of electrons or a negative charge with an associated cation.

3. The compound of claim 2 wherein R is hydrogen, substituted or unsubstituted alkyl or substituted or unsubstituted alkoxycarbonyl, W is hydrogen or halo, and Y is hydroxy, mercapto or amino.

4. A reducible compound of the structure CAR-$(-R^1)_n$ wherein CAR- is a substituted or unsubstituted aromatic or quinone nucleus, n is 1 or 2, and $R^1$ comprises a fluorescent moiety derived from a substituted or unsubstituted compound represented by the structure:

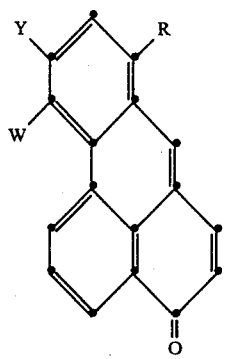

wherein R is hydrogen, substituted or unsubstituted alkyl, substituted or unsubstituted hydroxyalkyl or substituted or unsubstituted alkoxycarbonyl, W is hydrogen or an electron withdrawing group, and Y is hydroxy or mercapto.

5. The reducible compound of claim 4 wherein R is hydrogen, substituted or unsubstituted alkyl or substituted or unsubstituted alkoxycarbonyl, W is hydrogen or halo, and Y is hydroxy.

6. The reducible compound of claim 4 wherein CAR- is represented by the structure:

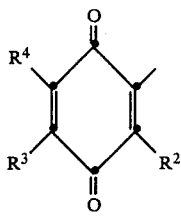

$R^1$ is

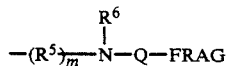

$R^2$ and $R^4$ are independently hydrogen, substituted or unsubstituted alkyl, substituted or unsubstituted aryl or an electron withdrawing group, $R^3$ is $R^1$, hydrogen, substituted or unsubstituted alkyl, substituted or unsubstituted aryl or an electron withdrawing group, or $R^3$ and $R^4$, taken together, represent the atoms necessary to complete a substituted or unsubstituted fused carbocyclic ring, $R^5$ is substituted or unsubstituted alkylene of 1 or 2 carbon atoms, $R^6$ is substituted or unsubstituted alkyl, substituted or unsubstituted cycloalkyl, substituted or unsubstituted heterocycle or substituted or unsubstituted aryl, Q is carbonyl or thiocarbonyl, FRAG is said fluorescent moiety, and m is 0 or 1.

7. An aqueous composition buffered at a pH of 9 or less and comprising the reducible compound of claim 4.

8. A hydrolyzable compound represented by the structure:

BLOCK-X-R$^f$-L, wherein BLOCK is a hydrolyzable group, X is —O—, —NR'—, or —S—, R' is hydrogen, substituted or unsubstituted alkyl, substituted or unsubstituted cyclohexyl, substituted or unsubstituted phenyl or a substituted or unsubstituted heterocyclic group, R$^f$ is a moiety derived from a substituted or unsubstituted compound represented by the structure:

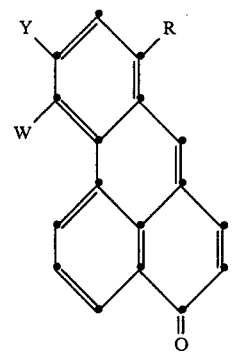

wherein R is hydrogen, substituted or unsubstituted alkyl, substituted or unsubstituted hydroxyalkyl or substituted or unsubstituted alkoxycarbonyl, W is hydrogen or an electron withdrawing group, and Y is a group comprised of a heteroatom having a lone pair of electrons or a negative charge with an associated cation, and L is hydrogen or a specific binding ligand.

9. The hydrolyzable compound of claim 8 wherein BLOCK is -COR*, phosphono or thioxophosphono or a salt thereof or is derived from an amino acid, peptide, mono- or polysaccharide, wherein R* is hydrogen, substituted or unsubstituted alkyl, substituted or unsubstituted alkenyl, substituted or unsubstituted aryl, substituted or unsubstituted cycloalkyl, or a substituted or unsubstituted heterocyclic group.

10. The hydrolyzable compound of claim 9 wherein BLOCK is -COR* of phosphono.

11. The hydrolyzable compound of claim 8 wherein L is hydrogen and X is oxy or imino.

12. The hydrolyzable compound of claim 8 wherein L is a specific binding ligand.

* * * * *